(12) United States Patent
Church et al.

(10) Patent No.: US 10,179,932 B2
(45) Date of Patent: Jan. 15, 2019

(54) METHODS FOR HIGH-THROUGHPUT LABELLING AND DETECTION OF BIOLOGICAL FEATURES IN SITU USING MICROSCOPY

(71) Applicant: President and Fellows of Harvard College, Cambridge, MA (US)

(72) Inventors: George M. Church, Brookline, MA (US); Je-Hyuk Lee, Allston, MA (US); Evan R. Daugharthy, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/325,577

(22) PCT Filed: Jul. 10, 2015

(86) PCT No.: PCT/US2015/039914
§ 371 (c)(1),
(2) Date: Jan. 11, 2017

(87) PCT Pub. No.: WO2016/007839
PCT Pub. Date: Jan. 14, 2016

(65) Prior Publication Data
US 2017/0159136 A1   Jun. 8, 2017

Related U.S. Application Data

(60) Provisional application No. 62/023,226, filed on Jul. 11, 2014.

(51) Int. Cl.
| | | |
|---|---|---|
| *C12Q 1/6844* | (2018.01) | |
| *C07H 21/02* | (2006.01) | |
| *C07H 21/04* | (2006.01) | |
| *C12Q 1/6841* | (2018.01) | |

(52) U.S. Cl.
CPC .......... *C12Q 1/6841* (2013.01); *C07H 21/02* (2013.01); *C07H 21/04* (2013.01)

(58) Field of Classification Search
CPC combination set(s) only.
See application file for complete search history.

(56) References Cited

U.S. PATENT DOCUMENTS

| | | | |
|---|---|---|---|
| 5,563,056 | A | 10/1996 | Swan et al. |
| 7,323,305 | B2 | 1/2008 | Leamon et al. |
| 7,473,767 | B2 | 1/2009 | Dimitrov |
| 9,217,151 | B2 | 12/2015 | Yin et al. |
| 2002/0015952 | A1 | 2/2002 | Anderson et al. |
| 2003/0148335 | A1 | 8/2003 | Shen et al. |
| 2004/0248144 | A1 | 12/2004 | Mir |
| 2005/0147981 | A1 | 7/2005 | Yamakawa et al. |
| 2005/0233318 | A1 | 10/2005 | Chee et al. |
| 2006/0024711 | A1 | 2/2006 | Lapidus et al. |
| 2006/0177833 | A1 | 8/2006 | Brenner |
| 2006/0234261 | A1 | 10/2006 | Pierce et al. |
| 2006/0248349 | A1 | 11/2006 | Rathjen et al. |
| 2006/0292611 | A1 | 12/2006 | Berka et al. |
| 2007/0020650 | A1 | 1/2007 | Kahvejian |
| 2007/0087362 | A1 | 4/2007 | Church et al. |
| 2007/0117109 | A1 | 5/2007 | Rothemund |
| 2007/0117177 | A1 | 5/2007 | Luo et al. |
| 2009/0005259 | A1 | 1/2009 | Drmanac |
| 2009/0208965 | A1 | 8/2009 | Tafas et al. |
| 2009/0246879 | A1 | 10/2009 | Drmanac et al. |
| 2010/0009868 | A1 | 1/2010 | Yan et al. |
| 2010/0047924 | A1 | 2/2010 | Webster et al. |
| 2010/0223276 | A1 | 9/2010 | Al-Shameri et al. |
| 2010/0268478 | A1 | 10/2010 | Andregg et al. |
| 2011/0086774 | A1 | 4/2011 | Dunaway |
| 2011/0092376 | A1 | 4/2011 | Colston, Jr. et al. |
| 2011/0245111 | A1 | 10/2011 | Chee |
| 2011/0257031 | A1 | 10/2011 | Bodeau et al. |
| 2011/0294135 | A1 | 12/2011 | Carlson |
| 2012/0040397 | A1 | 2/2012 | Luo et al. |
| 2012/0122712 | A1 | 5/2012 | Goldstein |
| 2013/0245096 | A1 | 9/2013 | Abitbol |
| 2014/0087378 | A1 | 3/2014 | Chatre et al. |
| 2014/0220587 | A1 | 8/2014 | Green, Jr. et al. |
| 2015/0133319 | A1 | 5/2015 | Fu et al. |
| 2016/0265046 | A1 | 9/2016 | Zhang et al. |
| 2017/0212983 | A1 | 7/2017 | Cai et al. |

FOREIGN PATENT DOCUMENTS

| | | |
|---|---|---|
| KR | 20080003402 A | 1/2008 |
| WO | 9746704 A1 | 12/1997 |
| WO | 2007086900 A2 | 8/2007 |

(Continued)

OTHER PUBLICATIONS

Eliscovich et al. mRNA on the move: The road to its biological destiny. Journal of Biological Chemistry, vol. 288, No. 28, pp. 20361-20368, Jul. 2013, in press May 2013 (Year: 2013).*
Weiss et al. Protein targeting to subcellular organelles via mRNA localization. Biochimica et Biophysica Acta, vol. 1833, pp. 260-273, 2013, available online Apr. 2012 (Year: 2012).*
Jambhekar et al. Cis-acting determinants of asymmetric, cytoplasmic RNA transport. RNA, vol. 13, pp. 625-642, 2007 (Year: 2007).*
Singer-Kruger et al. Here, there, everywhere. RNA Biology, vol. 11, No. 8, pp. 1031-1039, Aug. 2014. (Year: 2014).*

(Continued)

*Primary Examiner* — Jennifer Dunston
(74) *Attorney, Agent, or Firm* — Banner & Witcoff, Ltd.

(57) ABSTRACT

Methods of labelling one or more subcellular components (e.g., an organelle and/or subcellular region) in vivo are provided. Methods of labelling a protein in vivo are provided. Methods of determining a nucleic acid sequence in situ are also provided.

19 Claims, 6 Drawing Sheets
(5 of 6 Drawing Sheet(s) Filed in Color)
Specification includes a Sequence Listing.

(56) References Cited

FOREIGN PATENT DOCUMENTS

| WO | 2007/121489 A2 | 10/2007 |
| WO | 2008069973 A2 | 6/2008 |
| WO | 2009046149 A1 | 4/2009 |
| WO | 2010080134 A1 | 7/2010 |
| WO | 2011/143583 A1 | 11/2011 |
| WO | 2012005595 A2 | 1/2012 |
| WO | 2012/058638 A2 | 5/2012 |
| WO | 2012150035 A1 | 11/2012 |
| WO | 2013/055995 A2 | 4/2013 |
| WO | 2014/0163886 A1 | 10/2014 |
| WO | 2014/182528 A2 | 11/2014 |
| WO | 2015/118029 A1 | 8/2015 |

OTHER PUBLICATIONS

Matlin et al. Spatial expression of the genome: the signal hypothesis at forty. Nature Reviews. Molecular Cell Biology, vol. 12, No. 5, pp. 333-340, May 2011, Epub Apr. 2011. (Year: 2011).*

Polidoros et al. Rolling circle amplification—RACE: a method for simultaneous isolation of 5' and 3' cDNA ends from amplified cDNA templates. BioTechniques, vol. 41, No. 1, pp. 35, 36, 38 and 40, Jul. 2006, including p. 1/1 of Supplementary Material. (Year: 2006).*

Tsaftaris et al. Isolation of three homologous AP1-like MADS-box genes in crocus (*Crocus sativus* L.) and characterization of their expression. Plant Science, vol. 166, No. 5, pp. 1235-1243, May 2004. (Year: 2004).*

Meeks et al. Characterization of genes encoding poly(A) polymerases in plants: Evidence for duplication and functional specialization. PLoS ONE, vol. 4, No. 11, e8082, Nov. 2009, printed as pp. 1/10-10/10. (Year: 2009).*

Kalivas et al. famRCA-RACE: A rolling circle amplification RACE for isolating a family of homologous cDNAs in one reaction . . . Preparative Biochemistry and Biotechnology, vol. 40, No. 3, pp. 177-187, Jul. 2010. (Year: 2010).*

Ascano, M et al. Identification of RNA-Protein Interaction Networks Using PAR-CLIP. Wiley Interdiscip Rev RNA. Mar. 2012, vol. 3, No. 2; pp. 159-177; p. 3, third paragraph; p. 16, figure 1; p. 25, figure 6; DOI: 10.1002/wrna.1103.

Ginart, P et al. RNA Sequencing In Situ. Nat Biotechnol. Jun. 2014, vol. 32, No. 6; pp. 543-544; DOI: 10.1038/nbt.2921.

Lee, JH et al. Highly Multiplexed Subcellular RNA Sequencing In Situ. Science. Mar. 21, 2014, vol. 343, No. 6177; pp. 1360-1363; abstract; p. 1360, second column, second paragraph to third column, first paragraph; p. 1361, first column, first paragraph; p. 1363, first column, second paragraph to second column, first paragraph; DOI: 10.1126/science.1250212, and pp. 1/33-33/33 of Supplementary Materials.

Saliba, AE et al. Single-Cell RNA-Seq: Advances and Future Challenges. Nucleic Acids Res. Jul. 22, 2014, vol. 42, No. 14; pp. 8845-8860; DOI: 10.1093/nar/gku555.

Dec. 18, 2014 (PCT) International Preliminary Report—App PCT/US2013/044241.

Benner et al. "Gene Expression analysis by massively parallel signature sequencing (MPSS) on microbead arrays". Nature Biotechnology, vol. 18, pp. 630-634 (Jun. 31, 2000).

Brenner, et al. "Gene expression analysis by massively parallel signature sequencing (MPSS) on microbead arrays". Nature Biotechnology vol. 18, pp. 630-634 (2000) doi:10.1038/76469.

Extended European Seach Report issued in corresponding European Application No. 12860433.7, dated Aug. 13, 2015.

Grompe (1993) Nature Genetics DOI: 10.1038/ng1093-111.

Han et al. "Quantum-dot-tagged microbeads for multiplexed optical coding of biomolecules". Nature Biotechnology, vol. 19, 99. 631-635 (Jul. 31, 2001).

International Search Report and Written Opinion issued in corresponding International Application No. PCT/US2012/071398, dated Apr. 8, 2013.

Office Action issued for corresponding European Patent Application No. 12780609.9, dated Sep. 23, 2015.

Seo, et al. Four-color DNA sequencing by synthesis on a chip using photocleavable fluorescent nucleotides. Proceeding of the National Academy of Sciences, Apr. 2005, 102 (17) 5926-5931.

Shendure Jay et al., "Accurate multiplex polony sequencing of an evolved bacterial genome," Science, American Association for the Advancement of Science, Washington, DC; US, vol. 309, No. 5741, Sep. 1, 2005, pp. 1728-1732, XP002427180, ISSN: 0036-8075, DOI: 10.1126/SCIENCE.1117839.

Thisse et al. "High-Resolution in situ hybridization to whole-mount zebrafish embryos" 2008. Nature Protocols. vol. 3 No. 1 pp. 59-69. Doi:10.1038/nprot.2007.514.

Thisse et al. 2008 Nature protocols vol. 3 No. 1 pp. 59-69. Doi:10.1038/nprot.2007.514.

* cited by examiner

METHODS FOR HIGH-THROUGHPUT LABELLING AND DETECTION OF BIOLOGICAL FEATURES IN SITU USING MICROSCOPY

RELATED APPLICATION DATA

This application claims priority to U.S. Provisional Patent Application No. 62/023,226, filed on Jul. 11, 2014 and is hereby incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on May 11, 2018, is named 010498_00899 SL.txt and is 2,311 bytes in size.

STATEMENT OF GOVERNMENT INTERESTS

This invention was made with Government support under grant number 1U01MH098977-01 awarded by NIMH, grant number DE-FG02-02ER63445 awarded by DOE, and R01 MH103910-01 awarded by NHGRI. The Government has certain rights in the invention.

FIELD

The present invention relates to methods and compositions for detecting, identifying, measuring, counting, and/or segmenting biological features in cells.

BACKGROUND

Current methods for detecting biological features in cells broadly fall into three categories: 1) affinity-based detection using synthetic or natural antibodies conjugated to a fluorescent moiety; 2) fusing biological features to recombinant fluorescent proteins; and 3) labelling biological features with dyes. These art-known methods enable quantitative detection and localization of target features in fixed and/or living cells in situ. However, methods known in the art at the time of filing suffer from the drawback of only being able to utilize a narrow range of spectral space for multiplexed detection. Further, methods known in the art at the time of filing are prone to artifacts due to e.g., autofluorescence and/or noise in the analog signal domain.

SUMMARY

Accordingly, novel compositions and methods for specifically labelling of biological features in living cells, followed by detection of associated barcodes in situ using fluorescent sequencing are provided.

Embodiments of the present invention are directed to methods that are broadly applicable to highly specific multiplex visualization and localization of biological features. Unlike technologies known by others in the art at the time of filing, such as e.g., the use of fluorescent proteins, antibodies, nucleic acid probes, and the like, the methods of the present invention provide a subset of possible sequences that can be used to identify individual features. By applying a sequence pattern identification and matching approach to object-based image analysis, the methods described herein enable very high multiplexing capacity, while effectively eliminating false positives due to autofluorescence and background noise. Biological features (e.g., proteins and nucleic acids, macromolecular complexes, subcellular structures, cells, cell projections, extracellular structures, cell populations, tissue regions, organs, and other biological structures of interest) can be easily identified without relying on low-throughput, manual annotation or traditional automated image processing methods having limited sensitivity and/or accuracy.

In certain exemplary embodiments, a method of labelling a subcellular component in vivo is provided. The method includes the steps of providing a cell expressing an RNA comprising a barcode, reverse transcribing the RNA to produce DNA, circularizing the DNA, and performing rolling circle amplification (RCA) to produce an amplicon. The method optionally includes the step of detecting the amplicon.

In certain aspects, the RNA comprises a localization sequence that targets the RNA to the subcellular component. In other aspects, the subcellular component is an organelle (e.g., one or any combination of a nucleus, a nucleolus, a mitochondria, a Golgi apparatus, an endoplasmic reticulum, a ribosome, a lysosome, a vacuole, an endocytic vesicle, an exocytic vesicle, a cytoskeleton and a chloroplast) or a subcellular region (e.g., of one or any combination of a plasma membrane, a cell wall and a ribosomal subunit). In still other aspects, expression of the RNA is controlled by a promoter selected from the group consisting of one or any combination of an inducible promoter, a cell type-specific promoter and a signal-specific promoter. In certain aspects, a promoter is an endogenous promoter. In other aspects, a promoter is an exogenous promoter.

In certain exemplary embodiments, a method of labelling a protein in vivo is provided. The method includes the steps of providing a cell that expresses an RNA comprising a barcode and that expresses a protein comprising an RNA binding domain, allowing the RNA and the protein to interact, reverse transcribing the RNA to produce DNA, circularizing the DNA, and performing RCA to produce an amplicon. The method optionally includes the step of detecting the amplicon.

In certain aspects, the protein further comprises a domain that localizes it to a subcellular component. The subcellular component can be an organelle (e.g., one or any combination of a nucleus, a nucleolus, a mitochondria, a Golgi apparatus, an endoplasmic reticulum, a ribosome, a lysosome, a vacuole, an endocytic vesicle, an exocytic vesicle, a cytoskeleton and a chloroplast) or a subcellular region (e.g., of one or any combination of a plasma membrane, a cell wall and a ribosomal subunit). In other aspects, expression of the RNA is controlled by a promoter selected from the group consisting of one or any combination of an inducible promoter, a cell type-specific promoter and a signal-specific promoter. In certain aspects, a promoter is an endogenous promoter. In certain aspects, a promoter is an exogenous promoter.

In certain exemplary embodiments, a method of determining a nucleic acid sequence in situ is provided. The method includes the steps of providing a cell expressing an RNA comprising a barcode, reverse transcribing the RNA to produce DNA, circularizing the DNA, performing RCA to produce an amplicon, and sequencing the amplicon. In certain aspects, the cell further expresses a protein comprising an RNA binding domain.

BRIEF DESCRIPTION OF THE DRAWINGS

The patent or application file contains drawings executed in color. Copies of this patent or patent application publication with the color drawings will be provided by the Office upon request and payment of the necessary fee. The foregoing and other features and advantages of the present invention will be more fully understood from the following detailed description of illustrative embodiments taken in conjunction with the accompanying drawings in which:

FIGS. 1A-1B schematically depict sequencing-compatible rolling circle amplification (RCA) amplicons crosslinked to a cell matrix and/or protein. (1A) A protein of interest is fused to a specific RNA binding protein (e.g., MS2, phage N peptides or the like) either at the N-terminus, the C-terminus or internally. A barcode-bearing RNA molecule with a stem-loop sequence that imparts high specificity binding is co-expressed in the cell. (1B) Cells are fixed and reverse transcription from internally primed stem loop RNA structures is used to convert RNA to DNA.

FIG. 2 schematically depicts a method for efficiently generating DNA amplicons from bar code-bearing RNA molecules according to certain aspects of the invention. Synthesis of DNA from complementary RNA in situ is improved by using the end of the stem-loop structure, which also serves as the recognition site for the RNA binding protein. After reverse transcription (RT), RNases are used to remove much of the RNA, while an additional cleavage step is performed using a guide oligo and a restriction enzyme that processes the 5' end of the DNA for efficient circularization. RCA is then used to generate tandem copies of the DNA, enabling molecular sequencing in situ with a high signal-to-noise ratio. The figure discloses transcript sequences as SEQ ID NOS 1 and 2; RT sequences as SEQ ID NOS 1, 3, and 4; RNase H sequences as SEQ ID NOS 5 and 4; Guide oligo hybridization sequences as SEQ ID NOS 3 and 4; Dpn II digestion sequences as SEQ ID NOS 6 and 4; and circularization sequence as SEQ ID NO: 7, all respectively, in order of appearance, identified in the 5' to 3' orientation.

DETAILED DESCRIPTION OF CERTAIN EMBODIMENTS

The present invention provides methods for detecting biological features in situ utilizing nucleic acid barcodes sequences. In certain exemplary embodiments, a cell expresses an exogenous nucleic acid sequence, e.g., an RNA sequence, that comprises a barcode. The barcode can serve as a label for the cell itself, and/or as a label for a subcellular component, e.g., an organelle or subcellular region of the cell. In certain aspects, the RNA sequence further comprises one or more localization sequences that direct RNA to one or more processing pathways (e.g., endogenous and/or exogenous) to localize the RNA sequence such that it can function as a barcode label for subcellular or extracellular features.

As used herein, the term "barcode" refers to a unique oligonucleotide sequence that allows a corresponding nucleic acid sequence (e.g., an oligonucleotide fragment) to be identified, retrieved and/or amplified. In certain embodiments, barcodes can each have a length within a range of from 4 to 36 nucleotides, or from 6 to 30 nucleotides, or from 8 to 20 nucleotides. In certain exemplary embodiments, a barcode has a length of 4 nucleotides. In certain aspects, the melting temperatures of barcodes within a set are within 10° C. of one another, within 5° C. of one another, or within 2° C. of one another. In other aspects, barcodes are members of a minimally cross-hybridizing set. That is, the nucleotide sequence of each member of such a set is sufficiently different from that of every other member of the set that no member can form a stable duplex with the complement of any other member under stringent hybridization conditions. In one aspect, the nucleotide sequence of each member of a minimally cross-hybridizing set differs from those of every other member by at least two nucleotides. Barcode technologies are known in the art and are described in Winzeler et al. (1999) Science 285:901; Brenner (2000) Genome Biol. 1:1 Kumar et al. (2001) Nature Rev. 2:302; Giaever et al. (2004) Proc. Natl. Acad. Sci. USA 101:793; Eason et al. (2004) Proc. Natl. Acad. Sci. USA 101:11046; and Brenner (2004) Genome Biol. 5:240.

As used herein, the term "nucleic acid" includes the term "oligonucleotide" or "polynucleotide" which includes a plurality of nucleotides. The term "nucleic acid" is intended to include naturally occurring nucleic acids and synthetic nucleic acids. The term "nucleic acid" is intended to include single stranded nucleic acids and double stranded nucleic acids. The term "nucleic acid" is intended to include DNA and RNA, whether single stranded or double stranded. Nucleotides of the present invention will typically be the naturally-occurring nucleotides such as nucleotides derived from adenosine, guanosine, uridine, cytidine and thymidine. When oligonucleotides are referred to as "double-stranded," it is understood by those of skill in the art that a pair of oligonucleotides exists in a hydrogen-bonded, helical array typically associated with, for example, DNA. In addition to the 100% complementary form of double-stranded oligonucleotides, the term "double-stranded" as used herein is also meant to include those form which include such structural features as bulges and loops (see Stryer, Biochemistry, Third Ed. (1988), incorporated herein by reference in its entirety for all purposes). As used herein, the term "polynucleotide" refers to a strand of nucleic acids that can be a variety of different sizes. Polynucleotides may be the same size as an oligonucleotide, or may be two-times, three-times, four-times, five-times, ten-times, or greater than the size of an oligonucleotide.

Oligonucleotides and/or polynucleotides may be isolated from natural sources or purchased from commercial sources. Oligonucleotide and/or polynucleotide sequences may be prepared by any suitable method, e.g., the phosphoramidite method described by Beaucage and Carruthers ((1981) Tetrahedron Lett. 22: 1859) or the triester method according to Matteucci et al. (1981) J. Am. Chem. Soc. 103:3185), both incorporated herein by reference in their entirety for all purposes, or by other chemical methods using either a commercial automated oligonucleotide synthesizer or high-throughput, high-density array methods described herein and known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

As used herein, the term "cellular component" refers to a portion of a prokaryotic or eukaryotic cell. A cellular component includes, for example, a cellular organelle, including, but not limited to, a nucleus, a nucleolus, a mitochondria, a Golgi apparatus, an endoplasmic reticulum, a ribosome, a lysosome, a vacuole, an endocytic vesicle, an exocytic vesicle, a vacuole, a cytoskeleton, a chloroplast, and the like. A cellular component can also include a subcellular region, including, but not limited to, a plasma membrane, cell wall, a ribosomal subunit, transcriptional machinery, cell projections, and the like.

In certain embodiments, cells expressing an exogenous RNA sequence also express one or more polypeptides comprising an RNA binding domain. RNA binding domains include four main families: RNA recognition motifs (RRMs), zinc fingers, KH domains and double-stranded RNA binding motifs (dsRBMs). (For a review, see Clery and Allain in Madam Curie Bioscience Database (2011), found at the ncbi[dot]nlm[dot]nih[dot]gov website.) Exemplary RNA binding domains include, but are not limited to, MS2, phage N peptides (such as, e.g., lambda phage or P22 phage N-peptides), and the like. A database of DNA binding domains suitable for use in the present invention can be found at the website rbpdb[dot]ccbr[dot]utoronto[dot]ca.

In certain aspects, the polypeptide is a nuclear, cytosolic or transmembrane protein or a portion thereof (e.g., a polypeptide), fused to one or more RNA binding domains, such that the RNA sequence can function as a barcode label for the fusion protein, allowing for highly parallel detection of proteins. The cellular origin of each RNA-barcode-bound fusion protein can be identified by sequencing the associated RNA barcode.

As used herein, the terms "peptide" and "polypeptide" include compounds that consist of two or more amino acids that are linked by means of a peptide bond. Peptides and polypeptides may have a molecular weight of less than 10,000 Daltons, less than 5,000 Daltons, or less than 2,500 Daltons. The terms "peptide" and "polypeptide" also include compounds containing both peptide and non-peptide components, such as pseudopeptide or peptidomimetic residues or other non-amino acid components. Such compounds containing both peptide and non-peptide components may also be referred to as a "peptide analogue" or a "polypeptide analogue."

As used herein, the term "protein" includes compounds that consist of amino acids arranged in a linear chain and joined together by peptide bonds between the carboxyl and amino groups of adjacent amino acid residues.

As used herein, the terms "attach" or "bind" refer to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in Molecular Biology of the Cell, 3d edition, Garland Publishing, 1994, incorporated herein by reference in its entirety for all purposes.

In certain exemplary embodiments, biological features can be labelled as described herein using 4N unique RNA barcodes, wherein N is sequence length. Cellular components labelled as described herein can be identified by sequencing one or more associated RNA barcode labels. When a transmembrane protein is labelled, the membrane borders of 4N (wherein N is sequence length) cells can uniquely be identified using the RNA barcode for highly multiplexed membrane segmentation.

In certain exemplary embodiments, one or more components involved with intracellular or intercellular communication (e.g., involved with synapse formation, vesicle trafficking and the like) can be labelled by expressing a fusion protein encoding a localization domain specific to both the component and to an RNA binding domain in a cell. The expressed RNA barcode label can bind the fusion protein and be subsequently transported to a cellular component (e.g., organelle or subcellular region) of interest.

In accordance with certain examples, methods of sequencing barcodes in situ within an organism (e.g., in a cell or subcellular component (e.g., an organelle or a subcellular region)) are provided. General sequencing methods known in the art, such as sequencing by extension with reversible terminators, fluorescent in situ sequencing (FISSEQ), pyrosequencing, massively parallel signature sequencing (MPSS) and the like (described in Shendure et al. (2004) Nat. Rev. 5:335, incorporated herein by reference in its entirety), are suitable for use with the matrix in which the nucleic acids are present. Reversible termination methods use step-wise sequencing-by-synthesis biochemistry that coupled with reversible termination and removable fluorescence (Shendure et al. supra and U.S. Pat. Nos. 5,750,341 and 6,306,597, incorporated herein by reference.

FISSEQ is a method whereby DNA is extended by adding a single type of fluorescently-labelled nucleotide triphosphate to the reaction, washing away unincorporated nucleotide, detecting incorporation of the nucleotide by measuring fluorescence, and repeating the cycle. At each cycle, the fluorescence from previous cycles is bleached or digitally subtracted or the fluorophore is cleaved from the nucleotide and washed away. FISSEQ is described further in Mitra et al. (2003) Anal. Biochem. 320:55, incorporated herein by reference in its entirety for all purposes.

Pyrosequencing is a method in which the pyrophosphate (PPi) released during each nucleotide incorporation event (i.e., when a nucleotide is added to a growing polynucleotide sequence). The PPi released in the DNA polymerase-catalyzed reaction is detected by ATP sulfurylase and luciferase in a coupled reaction which can be visibly detected. The added nucleotides are continuously degraded by a nucleotide-degrading enzyme. After the first added nucleotide has been degraded, the next nucleotide can be added. As this procedure is repeated, longer stretches of the template sequence are deduced. Pyrosequencing is described further in Ronaghi et al. (1998) Science 281:363, incorporated herein by reference in its entirety for all purposes.

MPSS utilizes ligation-based DNA sequencing simultaneously on microbeads. A mixture of labelled adaptors comprising all possible overhangs is annealed to a target sequence of four nucleotides. The label is detected upon successful ligation of an adaptor. A restriction enzyme is then used to cleave the DNA template to expose the next four bases. MPSS is described further in Brenner et al. (2000) Nat. Biotech. 18:630, incorporated herein by reference in its entirety for all purposes.

According to certain aspects, the barcodes within the organism or portion thereof can be interrogated in situ using methods known to those of skill in the art including fluorescently labelled oligonucleotide/DNA/RNA hybridization, primer extension with labelled ddNTP, sequencing by ligation and sequencing by synthesis. Ligated circular padlock probes described in Larsson, et al., (2004), Nat. Methods 1:227-232 can be used to detect multiple sequence targets in parallel, followed by either sequencing-by-ligation, -synthesis or -hybridization of the barcode sequences in the padlock probe to identify individual targets.

According to one aspect, methods described herein produce a three dimensional nucleic acid amplicon within an organism or portion thereof which is stable, long-lasting and resistant, substantially resistant or partially resistant to enzymatic or chemical degradation. The three dimensional nucleic acid amplicon can be repeatedly interrogated using standard probe hybridization and/or fluorescence based sequencing. The three dimensional nucleic acid amplicon can be repeatedly interrogated with little or no signal degradation, such as after more than 50 cycles, and with little position shift, such as less than 1 μm per amplicon.

In certain aspects, the fusion protein substitutes for traditional reporter proteins, such as fluorescent reporter proteins (e.g., green fluorescent protein (GFP), mCherry, and the like) in fixed cells to perform multiplexed protein localization studies, in which barcode sequences, rather than a specific fluorescent signal, define the label. In certain aspects, the fusion protein can substitute or complement immunocytochemistry, in which barcode sequences, rather than a limited range of colors from secondary antibodies, are used to define the label.

In certain exemplary embodiments, digital images are generated by fluorescent sequencing of barcode labels that are combined to create a composite image, in which all channels and images over time are spatially registered. The composite image would then contain potential signals at each pixel, with real signals corresponding to nucleic acid sequences, which are distinguishable from objects not of interest (e.g. dirt, autofluorescence, and the like) by the nature and/or content of the sequence signals.

The nature of expected sequence patterns and the space of potential sequence patterns encompassing the barcode labels serve as a priori information in object-based image analysis algorithms to identify objects and measure object attributes. Object identification does not rely on algorithms utilizing intensity-based thresholds, high signal-to-noise ratio, or other object features such as shape. Thus, it is much more sensitive for quantitative detection of molecular analytes or cellular features.

The variable region of an RNA comprising a barcode sequence may be generated randomly or may be designed. Variable regions can be constructed using nucleic acid synthesis methods or in vivo by recombination. An RNA comprising a barcode sequence can contain 'error-correcting' sequences to compensate for a possible sequencing error. An RNA comprising a barcode sequence may contain on or more RNA localization signals to the direct the cell to localize the RNA barcode molecules to specific subcellular and/or extracellular regions. An RNA comprising a barcode sequence can be polyadenylated to promote efficient nuclear export.

In certain exemplary embodiments, RNA-binding proteins as described further herein (e.g., MS2, lambda N peptide, P22 N peptide, and the like) or a portion thereof are fused in frame to a protein of interest at the N-terminus or the C-terminus end. These peptides are capable of binding their cognate sequence (e.g., a conserved RNA hairpin stem sequences) with high affinity. A protein of interest can be cytosolic, nuclear, or membrane-spanning, bearing a protein localization signal (i.e. cadherin, synapsin, histone, transcription factors). A protein of interest can be expressed by integrating or epi-chromosomal expression vectors delivered, e.g., by transfection or viral infection.

An RNA comprising a barcode sequence may be converted into cDNA by endogenous or exogenous biochemical means. The 3' end of an RNA comprising a barcode sequence can contain an RNA stem loop structure enabling efficient self-primed cDNA synthesis when cells are fixed and treated with a reverse transcription reaction mixture. The RNA:DNA hybrid formed after reverse transcription can be enzymatically processed using a combination nucleases and/or restriction enzymes, leaving single stranded cDNA of a fixed length, which can then be circularized and amplified by rolling circle amplification. The 3' an RNA comprising a barcode sequence end of the transcript can contain a RNA stem loop structure necessary for binding to e.g., MS2, phage N peptides, or any other sequence specific peptide domains.

In certain exemplary embodiments, an RNA:DNA complex is degraded and/or processed to yield a 5' phosphorylated single-stranded DNA molecule, allowing the cDNA barcode to be circularized, such as by enzymes like special DNA ligase sold under the trademark CircLigase. Rolling circle amplification can then be used to generate multiple tandem copies of the barcode in situ. Aminoallyl dUTP and crosslinkers can be to immobilize the amplicons, e.g., within an organism (e.g., in a cell or cellular component (e.g., an organelle or a subcellular region)). A primer complementary to the constant region of the barcode may be used to prime rolling circle amplification.

Certain aspects of the invention pertain to vectors, such as, for example, expression vectors. As used herein, the term "vector" refers to a nucleic acid sequence capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. By way of example, but not of limitation, a vector of the invention can be a single-copy or multi-copy vector, including, but not limited to, a BAC (bacterial artificial chromosome), a fosmid, a cosmid, a plasmid, a suicide plasmid, a shuttle vector, a P1 vector, an episome, YAC (yeast artificial chromosome), a bacteriophage or viral genome, or any other suitable vector. The host cells can be any cells, including prokaryotic or eukaryotic cells, in which the vector is able to replicate.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

In certain exemplary embodiments, an exogenous nucleic acid described herein (e.g., a nucleic acid sequence encoding an RNA having a barcode sequence and/or a nucleic acid sequence encoding a polypeptide (e.g., a fusion protein)) is expressed in bacterial cells using a bacterial expression vector such as, e.g., a fosmid. A fosmid is a cloning vector that is based on the bacterial F-plasmid. The host bacteria will typically only contain one fosmid molecule, although an inducible high-copy ori can be included such that a higher copy number can be obtained (e.g., pCC1FOS™, pCC2FOS™). Fosmid libraries are particularly useful for constructing stable libraries from complex genomes. Fosmids and fosmid library production kits are commercially available (EPICENTRE® Biotechnologies, Madison, Wis.). For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

In certain exemplary embodiments, the recombinant expression vectors comprise a nucleic acid sequence in a form suitable for expression of the nucleic acid sequence in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the foreign nucleic acid sequence encoding a plurality of ribonucleic acid sequences described herein is linked to the regulatory sequence(s) in a manner which allows for expression of the nucleic acid sequence. In certain aspects, operably linked nucleic acid sequences are physically linked, using e.g., fusion RNAs and/or fusion proteins without splicing and/or cleavage of the endogenous product and recombinant nucleic acid sequences. The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). It will be appreciated by those skilled in the art that the design of the expression vector can depend on such factors as the choice of the host cell to be transformed, the level of expression of protein desired, and the like.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, insect cells, fungal cells, archaeal cells, eubacterial cells, a virion, a virosome, a virus-like particle, a parasitic microbe, an infectious protein and the like. Cells include eukaryotic cells such as yeast cells, plant cells, and animal cells. Particular cells include bacterial cells. Other suitable cells are known to those skilled in the art.

Foreign nucleic acids (i.e., those which are not part of a cell's natural nucleic acid composition) may be introduced into a cell using any method known to those skilled in the art for such introduction. Such methods include transfection, transduction, infection (e.g., viral transduction), injection, microinjection, gene gun, nucleofection, nanoparticle bombardment, transformation, conjugation, by application of the nucleic acid in a gel, oil, or cream, by electroporation, using lipid-based transfection reagents, or by any other suitable transfection method. One of skill in the art will readily understand and adapt such methods using readily identifiable literature sources.

As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAMFECT™ (OZ Biosciences, France) and the like), or electroporation (e.g., in vivo electroporation). Suitable methods for transforming or transfecting host cells can be found in Sambrook, et al. (Molecular Cloning: A Laboratory Manual. 2nd, ed., Cold Spring harbor Laboratory, Cold Spring Harbor Laboratory Press, Cold Spring Harbor, N.Y., 1989), and other laboratory manuals.

Typically, the vector or plasmid contains sequences directing transcription and translation of a relevant gene or genes, a selectable marker, and sequences allowing autonomous replication or chromosomal integration. Suitable vectors comprise a region 5' of the gene which harbors transcriptional initiation controls and a region 3' of the DNA fragment which controls transcription termination. Both control regions may be derived from genes homologous to the transformed host cell, although it is to be understood that such control regions may also be derived from genes that are not native to the species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, lac, ara, tet, trp, IPL, IPR, T7, tac, and trc (useful for expression in *Escherichia coli* and *Pseudomonas*); the amy, apr, npr promoters and various phage promoters useful for expression in *Bacillus subtilis*, and *Bacillus licheniformis*; nisA (useful for expression in gram positive bacteria, Eichenbaum et al. Appl. Environ. Microbiol. 64(8):2763-2769 (1998)); and the synthetic P11 promoter (useful for expression in *Lactobacillus plantarum*, Rud et al., Microbiology 152:1011-1019 (2006)). Termination control regions may also be derived from various genes native to the preferred hosts.

In certain exemplary embodiments, an RNA comprising a barcode sequence can be expressed through transcription. Endogenous or exogenous promoters, such as U6 or H1, can drive expression of the RNA comprising a barcode sequence. The RNA comprising a barcode sequence may contain a common region for primer-based amplification and/or sequencing. The term RNA barcode may refer to a variable region alone or to both a variable and a common region, since in some instances the common region is used to provide a read-out of the variable region.

In certain exemplary embodiments, an RNA comprising a barcode sequence can be encoded by a genomic locus. In other exemplary embodiments, an RNA comprising a barcode sequence can be encoded by a vector. In certain aspects, an expression module is present in a fusion protein expression vector. In other exemplary embodiments, an RNA comprising a barcode sequence is delivered directly to a cell by transfection, in which a single RNA barcode oligonucleotide or a library of RNA barcode oligonucleotides is added exogenously.

Expression of an RNA comprising a barcode sequence can be signal-dependent and/or context-specific. For example, cell type-specific or signal-specific promoters can be used to express an RNA comprising a barcode sequence in a desired population of the cells so that only cellular components and/or proteins in responsive cells are labelled with the RNA comprising a barcode sequence. Expression of an RNA comprising a barcode sequence can be inducible (e.g., with doxycycline) in order to avoid toxic effects of prolonged single stranded RNA overexpression.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in gram negative bacteria (Scott et al., Plasmid 50(1):74-79 (2003)). Several plasmid derivatives of broad-host-range Inc P4 plasmid RSF1010 are also available with promoters that can function in a range of gram negative bacteria. Plasmid pAYC36 and pAYC37, have active promoters along with multiple cloning sites to allow for the heterologous gene expression in gram negative bacteria.

Chromosomal gene replacement tools are also widely available. For example, a thermosensitive variant of the broad-host-range replicon pWV101 has been modified to construct a plasmid pVE6002 which can be used to create gene replacement in a range of gram positive bacteria (Maguin et al., J. Bacteriol. 174(17):5633-5638 (1992)). Additionally, in vitro transposomes are available to create random mutations in a variety of genomes from commercial sources such as EPICENTRE® (Madison, Wis.).

Vectors useful for the transformation of *E. coli* are common and commercially available. For example, the desired genes may be isolated from various sources, cloned onto a modified pUC19 vector and transformed into *E. coli* host cells. Alternatively, the genes encoding a desired biosynthetic pathway may be divided into multiple operons, cloned into expression vectors, and transformed into various *E. coli* strains.

Features or objects may be of a biological nature, such as molecules, subcellular compartments, projections, cells, groups of cells, regions of tissue, tissues, or organs. Biological features may be made to have the characteristics described above by sequencing synthetic or natural, endogenous or exogenous, nucleic acid molecules spatially organized by any method, familiar to those with skill in the art.

Analysis of objects using methods described herein may be combined with or compared to other images of the sample that have been stained with membrane- and organelle-specific dyes, antibodies, or reporter proteins.

In certain embodiments, nucleic acids are those found naturally in a biological sample, such as a cell or tissue.

Embodiments of the present invention are directed to methods of amplifying nucleic acids in situ within an organism or portion thereof (e.g., cell (e.g., cellular component, e.g., organelle and/or subcellular region), tissue, organ or the like) by contacting the barcode with reagents and under suitable reaction conditions sufficient to amplify the barcode. According to one aspect, the organism or portion thereof is rendered porous or permeable to allow migration of reagents into the matrix to contact the barcode. In certain aspects, barcodes are amplified by selectively hybridizing an amplification primer to an amplification site at the 3' end of the barcode using conventional methods. Amplification primers are 6 to 100, and even up to 1,000, nucleotides in length, but typically from 10 to 40 nucleotides, although oligonucleotides of different length are of use.

Typically, selective hybridization occurs when two nucleic acid sequences are substantially complementary, i.e., at least about 65% 75%, 80%, 85%, 90%, 91%, 92%, 93%, 94%, 95%, 96%, 97%, 98% 99%, 99.1%, 99.2%, 99.3%, 99.4%, 99.5%, 99.6%, 99.7%, 99.8%, 99.9% or 100% complementary over a stretch of at least 14 to 25 nucleotides. See Kanehisa, M., 1984, Nucleic Acids Res. 12: 203, incorporated herein by reference in its entirety for all purposes.

Overall, five factors influence the efficiency and selectivity of hybridization of the primer to a second nucleic acid molecule. These factors, which are (i) primer length, (ii) the nucleotide sequence and/or composition, (iii) hybridization temperature, (iv) buffer chemistry and (v) the potential for steric hindrance in the region to which the primer is required to hybridize, are important considerations when non-random priming sequences are designed.

There is a positive correlation between primer length and both the efficiency and accuracy with which a primer will anneal to a target sequence; longer sequences have a higher Tm than do shorter ones, and are less likely to be repeated within a given target sequence, thereby cutting down on promiscuous hybridization. Primer sequences with a high G-C content or that comprise palindromic sequences tend to self-hybridize, as do their intended target sites, since unimolecular, rather than bimolecular, hybridization kinetics are generally favored in solution; at the same time, it is important to design a primer containing sufficient numbers of G-C nucleotide pairings to bind the target sequence tightly, since each such pair is bound by three hydrogen bonds, rather than the two that are found when A and T bases pair. Hybridization temperature varies inversely with primer annealing efficiency, as does the concentration of organic solvents, e.g., formamide, that might be included in a hybridization mixture, while increases in salt concentration facilitate binding. Under stringent hybridization conditions, longer probes hybridize more efficiently than do shorter ones, which are sufficient under more permissive conditions. Stringent hybridization conditions typically include salt concentrations of less than about 1M, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of any one alone. Hybridization conditions are known to those skilled in the art and can be found in Current Protocols in Molecular Biology, John Wiley & Sons, N.Y. (1989), 6.3.1-6.3.6, incorporated herein by reference in its entirety for all purposes.

Primers are designed with the above first four considerations in mind. While estimates of the relative merits of numerous sequences are made mentally, computer programs have been designed to assist in the evaluation of these several parameters and the optimization of primer sequences (see, e.g., Hoover et al. (2002) Nucleic Acids Res. 30:e43, and Rouillard et al. (2004) Nucleic Acids Res. 32:W176, incorporated by reference herein in their entirety for all purposes).

In accordance with an additional aspect, kits are provided. In one aspect, the kits comprise a cell described herein, and optionally, instructions for use.

According to one aspect, nucleic acids are modified to incorporate a functional moiety for attachment to a matrix. The functional moiety can be covalently crosslinked, copolymerize with or otherwise non-covalently bound to the matrix. The functional moiety can react with a crosslinker. The functional moiety can be part of a ligand-ligand binding pair. DNTP or dUTP can be modified with the functional group, so that the function moiety is introduced into the DNA during amplification. A suitable exemplary functional moiety includes an amine, acrydite, alkyne, biotin, azide, and thiol. In the case of crosslinking, the functional moiety is crosslinked to modified dNTP or dUTP or both. Suitable exemplary crosslinker reactive groups include imidoester (DMP), succinimide ester (NHS), maleimide (Sulfo-SMCC), carbodiimide (DCC, EDC) and phenyl azide. Crosslinkers within the scope of the present disclosure may include a spacer moiety. Such spacer moieties may be functionalized. Such spacer moieties may be chemically stable. Such spacer moieties may be of sufficient length to allow amplification of the nucleic acid bound to the matrix. Suitable exemplary spacer moieties include polyethylene glycol, carbon spacers, photo-cleavable spacers and other spacers known to those of skill in the art and the like.

According to one aspect, a matrix-forming material is contacted to a plurality of nucleic acids spatially arrange in three-dimensions relative to one another.

Matrix forming materials include polyacrylamide, cellulose, alginate, polyamide, crosslinked agarose, crosslinked dextran or crosslinked polyethylene glycol. The matrix forming materials can form a matrix by polymerization and/or crosslinking of the matrix forming materials using methods specific for the matrix forming materials and methods, reagents and conditions known to those of skill in the art. In certain aspects, the structure of a matrix is static, e.g., the matrix has a stable three-dimensional state. In other aspects, the matrix is flexible, e.g., one or more of matrix size, shape, etc. can be altered or modified such that higher spatial resolution is achieved and/or additional downstream analyses cab be performed, e.g., mass spectroscopy and the like.

According to one aspect, a matrix-forming material can be introduced into a cell. The cells are fixed with formaldehyde and then immersed in ethanol to disrupt the lipid membrane. The matrix forming reagents are added to the sample and are allowed to permeate throughout the cell. A polymerization inducing catalyst, UV or functional crosslinkers are then added to allow the formation of a gel matrix. The unincorporated material is washed out and any remaining functionally reactive group is quenched. Exemplary cells include any cell, human or otherwise, including diseased cells or healthy cells. Certain cells include human cells, non-human cells, human stem cells, mouse stem cells, primary cell lines, immortalized cell lines, primary and immortalized fibroblasts, HeLa cells and neurons.

According to one aspect, a matrix-forming material can be used to encapsulate a biological sample, such as a tissue sample. The formalin-fixed embedded tissues on glass slides are incubated with xylene and washed using ethanol to remove the embedding wax. They are then treated with Proteinase K to permeabilized the tissue. A polymerization inducing catalyst, UV or functional crosslinkers are then added to allow the formation of a gel matrix. The unincorporated material is washed out and any remaining functionally reactive group is quenched. Exemplary tissue samples include any tissue samples of interest whether human or non-human. Such tissue samples include those from skin tissue, muscle tissue, bone tissue, organ tissue and the like. Exemplary tissues include human and mouse brain tissue sections, embryo sections, tissue array sections, and whole insect and worm embryos.

The matrix-forming material forms a three dimensional matrix including the plurality of nucleic acids. According to one aspect, the matrix-forming material forms a three dimensional matrix including the plurality of nucleic acids while maintaining the spatial relationship of the nucleic acids. In this aspect, the plurality of nucleic acids are immobilized within the matrix material. The plurality of nucleic acids may be immobilized within the matrix material by co-polymerization of the nucleic acids with the matrix-forming material. The plurality of nucleic acids may also be immobilized within the matrix material by crosslinking of the nucleic acids to the matrix material or otherwise crosslinking with the matrix-forming material. The plurality of nucleic acids may also be immobilized within the matrix by covalent attachment or through ligand-protein interaction to the matrix.

According to one aspect, the matrix is porous thereby allowing the introduction of reagents into the matrix at the site of a nucleic acid for amplification of the nucleic acid. A porous matrix may be made according to methods known to those of skill in the art. In one example, a polyacrylamide gel matrix is co-polymerized with acrydite-modified streptavidin monomers and biotinylated DNA molecules, using a suitable acrylamide:bis-acrylamide ratio to control the crosslinking density. Additional control over the molecular sieve size and density is achieved by adding additional crosslinkers such as functionalized polyethylene glycols. According to one aspect, the nucleic acids, which may represent individual bits of information, are readily accessed by oligonucleotides, such as labelled oligonucleotide probes, primers, enzymes and other reagents with rapid kinetics.

According to one aspect, the matrix is sufficiently optically transparent or otherwise has optical properties suitable for standard Next Generation sequencing chemistries and deep three dimensional imaging for high throughput information readout. The Next Generation sequencing chemistries that utilize fluorescence imaging include a next-generation DNA sequencing technology sold under the trademark SoLiD (ABI Life Technologies), in which a sequencing primer on a template is ligated to a library of fluorescently labelled nonamers with a cleavable terminator. After ligation, the beads are then imaged using four color channels (FITC, Cy3, Texas Red and Cy5). The terminator is then cleaved off leaving a free-end to engage in the next ligation-extension cycle. After all dinucleotide combinations have been determined, the images are mapped to the color code space to determine the specific base calls per template. The overflow is achieved using an automated fluidics and imaging device (i.e. include a next-generation DNA sequencing technology sold under the trademark SoLiD 5500 W Genome Analyzer, ABI Life Technologies). Another sequencing platform uses sequencing by synthesis, in which a pool of single nucleotide with a cleavable terminator is incorporated using DNA polymerase. After imaging, the terminator is cleaved and the cycle is repeated. The fluorescence images are then analyzed to call bases for each DNA amplicons within the flow cell (a high-throughput sequencing system sold under the trademark HiSeq, Illumia).

According to certain aspects, the plurality of nucleic acids may be amplified to produce amplicons by methods known to those of skill in the art. The amplicons may be immobilized within the matrix generally at the location of the nucleic acid being amplified, thereby creating a localized colony of amplicons. The amplicons may be immobilized within the matrix by steric factors. The amplicons may also be immobilized within the matrix by covalent or noncovalent bonding. In this manner, the amplicons may be considered to be attached to the matrix. By being immobilized to the matrix, such as by covalent bonding or crosslinking, the size and spatial relationship of the original amplicons is maintained. By being immobilized to the matrix, such as by covalent bonding or crosslinking, the amplicons are resistant to movement or unraveling under mechanical stress.

According to one aspect, the amplicons, such as DNA amplicons, are then copolymerized and/or covalently attached to the surrounding matrix thereby preserving their spatial relationship and any information inherent thereto. For example, if the amplicons are those generated from DNA or RNA within a cell embedded in the matrix, the amplicons can also be functionalized to form covalent attachment to the matrix preserving their spatial information within the cell thereby providing a subcellular localization distribution pattern.

According to one aspect, a plurality of circular DNA molecules are covalently linked to one another. The circular DNA molecules are then amplified using methods known to those of skill in the art, such as isothermal enzymatic amplification one example of which is RCA. According to this aspect, the amplicons are localized near the circular DNA. According to this aspect, the amplicons form a shell around the circular DNA or otherwise assemble around the circular DNA. Each circular DNA may have more than 1000 amplicons surrounding or otherwise associated therewith. According to this aspect, the amplicons surrounding a particular circular DNA provide a high signal intensity, due in part to the number of amplicons and/or detectable labels associated with the amplicons.

The amplicons may be functionalized and crosslinked or otherwise covalently bound together around their associate circular DNA to form a series or network of tightly bound DNA amplicon shells around each circular DNA. The series or network of tightly bound DNA amplicon shells around each circular DNA may be assembled onto a three-dimensional support. According to one aspect, the series or network of tightly bound DNA amplicon shells around each circular DNA may be assembled onto a three-dimensional support producing a three dimensional DNA polymer with defined overall shape, size and amplicon position.

According to one aspect, amplicons are covalently linked without the need for separate crosslinkers, such as bis-N-succinimidyl-(nonaethylene glycol) ester. An acrydite moiety, such as a catalyst activated acrydite moiety is introduced at the end of a long carbon spacer (i.e., about C6 to about C12) at position 5 of a uracil base a representative formula of which is shown below.

In the formula below, R represents the acrydite spacer moiety attached to the 5 position of the uracil base.

When copolymerized with bis-acrylamide in the presence of a catalyst, a polymerization reaction takes place, encapsulating the circular DNA with the amplicons and fixing the amplicons in position. The chemically inert nature of the polymerized mixture allows various downstream applications. The spacer can be a carbon chain of between about 2 carbons to about 200 carbons. The spacer can be polyethylene glycol. The length of the spacer can vary from about 30 angstroms to about 100 angstroms and can be of various molecular weights. The spacer can be permanent or reversible, such as by using UV light, enzymes, chemical cleavage, etc.

A three dimensional matrix, such as a polyacrylamide gel matrix, can be used to embed a variety of biological structures containing enzymatically or chemically modified DNA or RNA molecules containing an acrydite functional moiety. The non-nucleic acid component is selectively dissolved using detergents, proteases, organic solvents or denaturants to create a three dimensional matrix that preserves individual DNA or RNA molecules and their relative spatial location. Examples include embedding cells, healthy and diseased tissues and tissue sections, small model organisms such as worms and insects, bacterial colonies or biofilms, environmental samples containing other DNA or RNA containing materials or organisms.

In certain exemplary embodiments, an object-based image analysis (OBIA) algorithm is used to analyze barcode sequences. The OBIA algorithm applies pattern identification and matching sequences to partition images into objects and measure object properties, given the objects are properly labelled with sufficiently long DNA or RNA barcode sequences. The actual sequence profile of an object is a subset of the total potential sequence space. Objects are identified through a priori information about the expected sequence patterns and the space of potential sequence patterns.

As used herein, a "digital image data" refers to a numeric representation of values corresponding to measured signals distributed in two- or three-dimensional space over time. The map may be stored using raster or vector format. The signals measured are generated using sequencing methods described above. Sequencing signals are characterized as a temporal pattern within the digital image data, such that the total signal profile is a subset of the total possible signal space. Digital image data can be processed using methods such as deconvolution, registration, normalization, projection, and/or any other appropriate mathematical transformations known in the art. Images are registered over time.

As used herein, the term "pattern identification OBIA" refers to the identification and characterization of an object within the image data by identifying the temporal pattern using prior information about the nature of expected patterns. According to this aspect of the invention, pixels are identified as objects or spatially clustered into objects by identifying pixels with the characteristics listed above. According to one aspect of the invention, objects are identified using the expectation that they consist of one or more spatially correlated pixels with a particular temporal sequence of signals.

As used herein, the term "pattern matching OBIA" refers to the identification and characterization of an object within the image data by matching the sequence patterns of individual pixels or composite patterns of groups of pixels to a reference set of expected patterns. In certain aspects of the invention, the patterns compared to the reference may be a subset of all patterns present in the image. In other aspects of the invention, all patterns in the data may be compared to the reference. According to certain aspects of the invention, patterns in the data may be compared and matched to the expected reference patterns by search methods and/or computation of distance metrics or probability functions familiar to those with skill in the art.

A reference characteristic may consist of nucleic acid sequences, including genomic or transcriptomic sequences as well as synthetic, artificial, or programmed sequences of nucleic acids. The reference characteristic may consist of any previously known set of patterns with the characteristics listed above.

Computational tasks related to OBIA are executed using the pattern identification and/or pattern matching methods, including feature recognition, segmentation, object tracking, object counting, object disambiguation, object reconstruction, and spatial classification. Sequence pattern identification and matching described above may be used for computational image processing tasks, such as image stitching, registration, filtering, colorization, parameterization, and noise reduction. For instance, objects in the digital image data with patterns not matched in the reference may be excluded from visualization and subsequent analysis. Remaining pixels may be false colored, filtered, or otherwise represented as a high-dynamic range image; with dynamic range sufficient to represent the space of identified sequences. This reduces the impact of autofluorescence and background noise from cellular debris in visualization and downstream analysis. Image registration and stitching algorithms can be designed to maximize the number of objects identified using methods described above.

Certain exemplary embodiments are directed to the use of computer software to automate design and/or interpretation of genomic sequences, mutations, oligonucleotide sequences and the like. Such software may be used in conjunction with individuals performing interpretation by hand or in a semi-automated fashion or combined with an automated system. In at least some embodiments, the design and/or interpretation software is implemented in a program written in the JAVA programming language. The program may be compiled into an executable that may then be run from a command prompt in the WINDOWS XP operating system. Unless specifically set forth in the claims, the invention is not limited to implementation using a specific programming language, operating system environment or hardware platform.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, tables and accompanying claims.

EXAMPLE I

RCA Amplicon Analysis

Figure 1A:
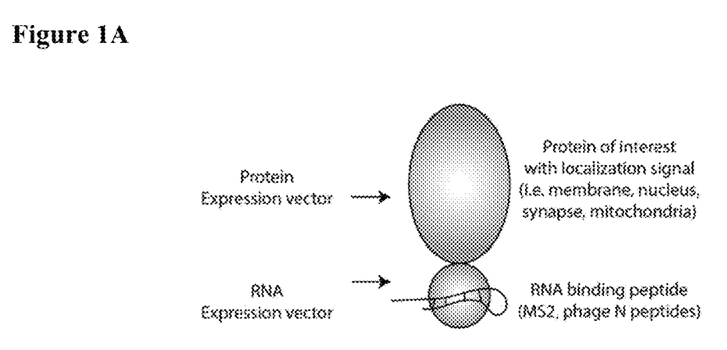
Figure 1B:
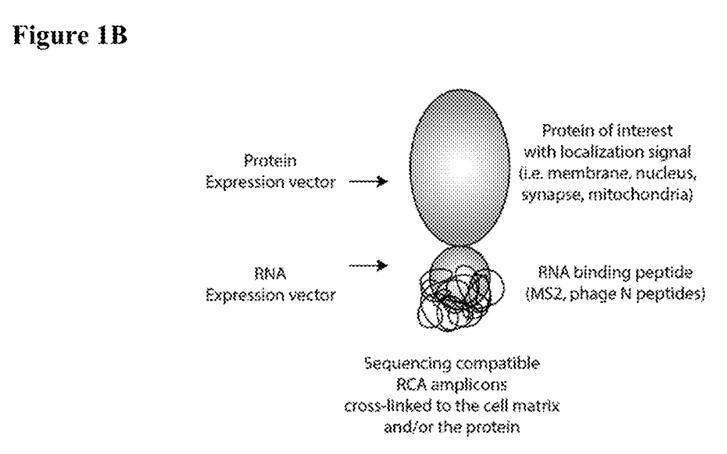
Figure 2:
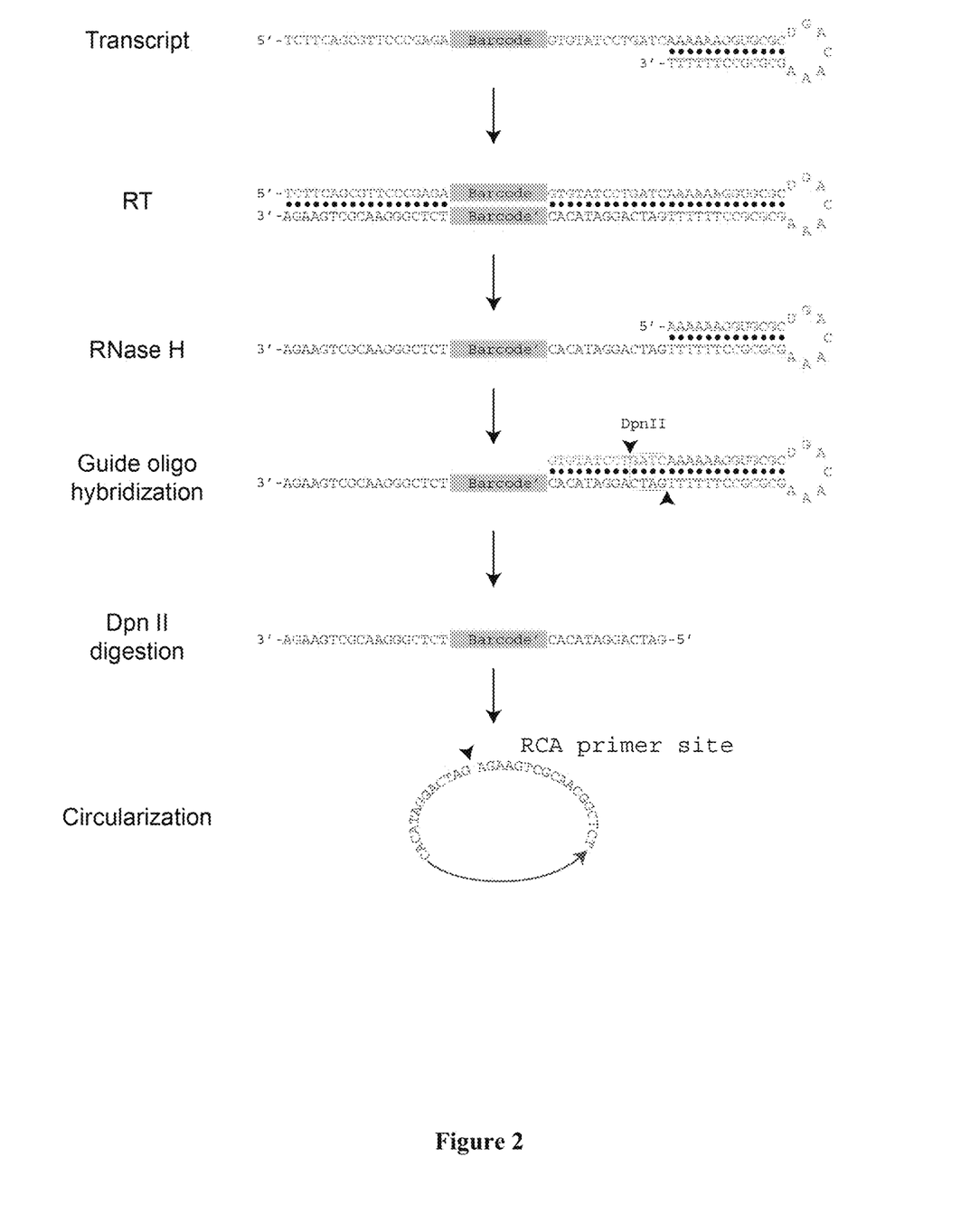
Figure 3:
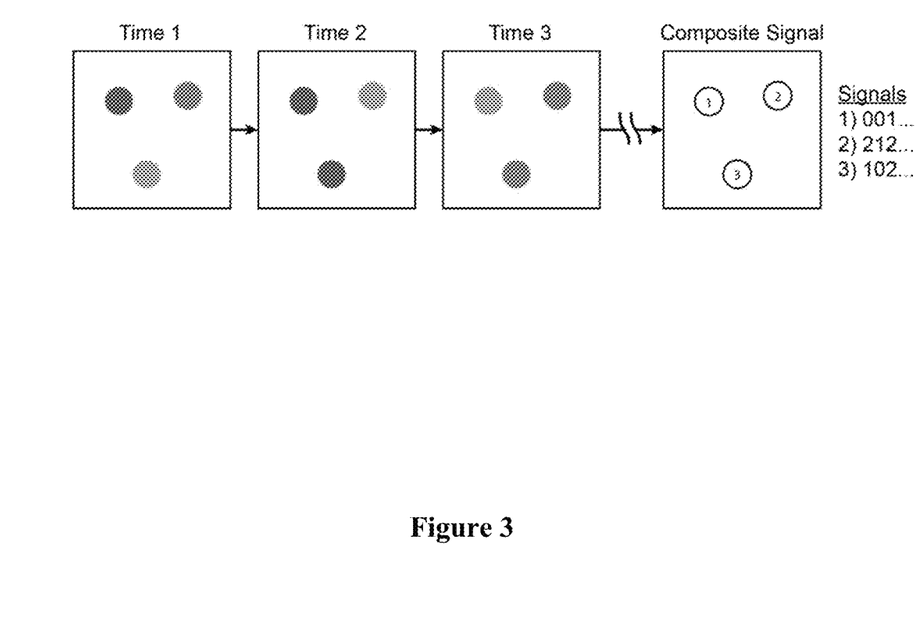
FIG. 3 schematically depicts digital images generated by fluorescent sequencing of barcode labels that are combined to create a composite image in which all channels and images over time are spatially registered. The composite image contains potential signals at each pixel. Real signals corresponding to nucleic acid sequences are distinguishable from objects not of interest (e.g., dirt, autofluorescence and the like) by the nature and/or content of the sequence signals. The nature of sequencing reactions can be programmed to give k signals per time point over N time points. Biological features can be labelled with kN unique barcodes.
Figure 4:
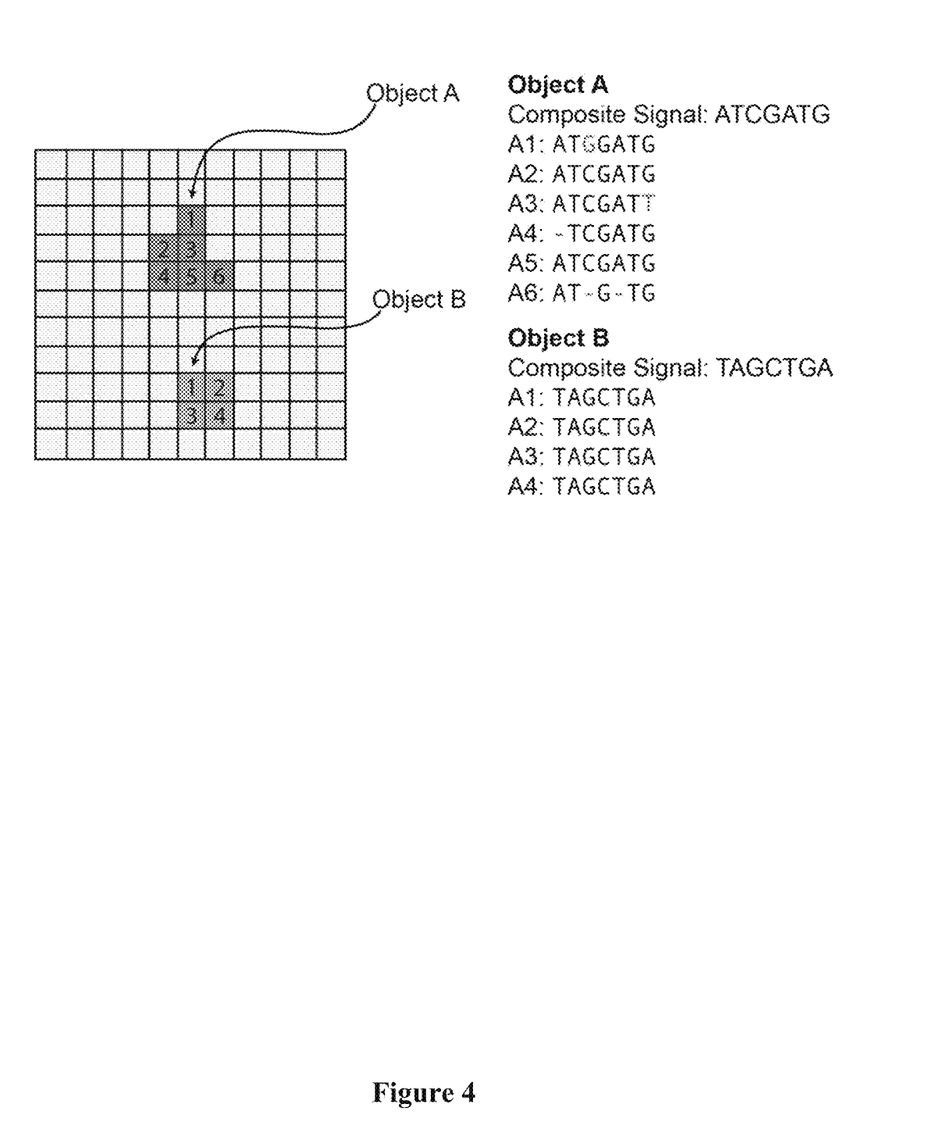
FIG. 4 schematically depicts the identification of two objects among the pixels of the image by the nature of their sequence patterns, i.e., they have signal at each sequencing base in only one channel, sustained over all sequencing reactions. The pixels constituting object A do not match each other perfectly, but a custom distance function clusters these as sufficiently similar to belong to the same object, and a composite sequence is generated. The pixels constituting object B each share identical sequences.
Figure 5:
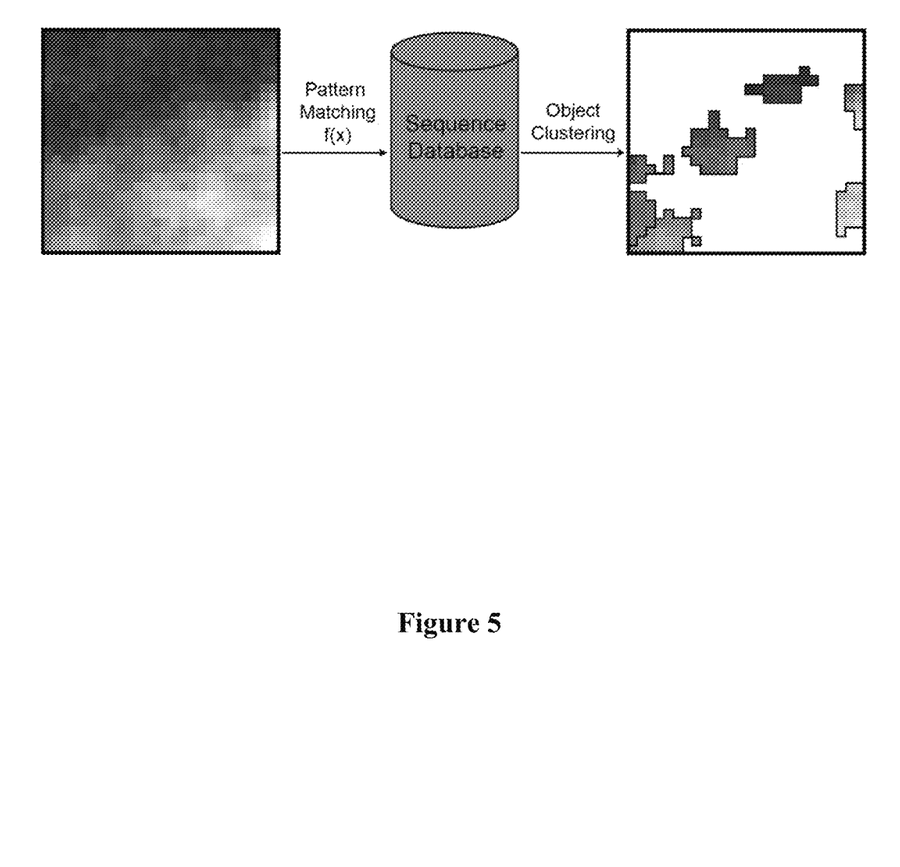
FIG. 5 schematically depicts the identification of objects by matching the sequence patterns in all pixels to a reference sequence database. Connected components (pixels) with shared sequences (or with shared matches to sequence patterns) are clustered to identify objects. Pixels without sequences in the reference sequence database are filtered out of the final image (e.g., background, noise, dirt, autofluorescence and the like). The attributes of each object, such as size, shape and genetic content, can be computed and used in downstream analyses.

A protein of interest is fused to a specific RNA binding protein and a barcode bearing RNA molecule is co-expressed in the cell (FIG. 1A). Cells are then fixed, and reverse transcribed from internally primed stem loop RNA structures are used to convert RNA to DNA (FIG. 1B). In certain aspects, the DNA is circularized using a special DNA ligase sold under the trademark CircLigase and amplified using Phi29 DNA polymerase. Crosslinker compatible nucleotides are incorporated during reverse transcription and rolling circle amplification. Crosslinkers can then be used to attach nucleotides to a subcellular component (e.g., the cell matrix and/or one or more proteins and/or attached to a synthetic three-dimensional support matrix (e.g., co-polymerized in an acrylamide gel). The single molecule amplicons are sequenced using direct DNA ligation, extension, or hybridization using fluorescently labelled probes. The sequential images from multiple sequencing or hybridization cycles are used to generate sequencing reads from each protein-RNA complex. The barcode sequence is then used to identify individual proteins and where the RNA is transcribed.

EXAMPLE II

Cell Segmentation

Cells expressing an RNA barcode widely throughout the cell body are labelled and segmented by using the barcode sequence to identify the space occupied by each cell.

EXAMPLE III

Multiplex Membrane Labelling

Using a fusion protein encoding membrane-specific proteins and cells that bear a single copy of the RNA barcode via site-specific recombination, a large number of cells are labelled with unique RNA barcodes localized to the cell membrane inner surface. This information, coupled with the use of complementary membrane dyes or proteins, enables a large number of cellular membranes to be uniquely identified and segmented. This allows one of ordinary skill in the art the ability to accurately assess single cell biology using, e.g., cell culture, tissue sections, and/or developing embryos.

EXAMPLE IV

Brain Synapse Mapping

Figure 6:
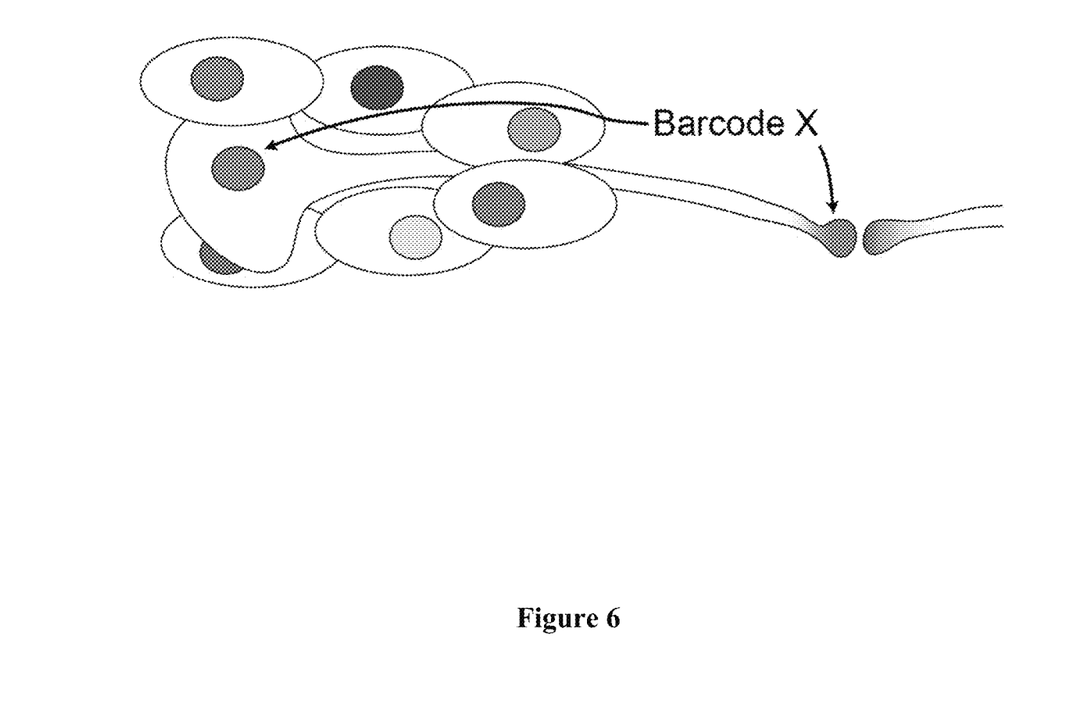
FIG. 6 schematically depicts neurons that are reconstructed using the methods described herein in which RNA barcodes are expressed in the nuclei or cell bodies, as well as in the synapse. Distant synapses are uniquely linked to the projecting cell body through the RNA barcode. The nuclear barcode is expressed but not polyadenylated, and is therefore localized to the nucleus without coupling to RNA-binding protein. The synapse is labelled with RNA barcode coupled to RNA-binding protein domain fused to a synapse-localizing proteins such as, e.g., neurexin.

By fusing the RNA binding domain to one or more pre-synaptic or post-synaptic proteins (e.g., neurexin, neuroligin, synapsin, NMDA receptor and the like) along with a cell-specific RNA barcode, the physical location of individual synapses and their cellular origins are imaged in a high-throughput manner. (See FIG. 6.) Each barcode also contains information regarding the identity of fusion proteins, such that a proper pairing of pre-synaptic and post-synaptic proteins can be identified using a co-localization matrix. In certain aspects, expression of the fusion protein and/or RNA barcode is activity-dependent, such that only those neurons and their synapses that are functionally active are imaged selectively. Synapses are then uniquely associated with the cells that generate them.

EXAMPLE V

Monitoring Intra-Cellular and/or Inter-Cellular Trafficking

RNA binding domains are specifically fused to vesicle-specific and/or exosome-specific proteins to track multiple vesicles and/or exosomes to their originating cells.

What is claimed is:

1. A method for identifying a protein of interest in a cell, comprising:
   (a) providing a cell comprising (i) a ribonucleic acid (RNA) molecule comprising a barcode and (ii) said protein of interest fused in frame to an RNA binding domain, wherein said RNA molecule binds to said RNA binding domain such that said RNA molecule localizes to said protein of interest in the cell;
   (b) within said cell, (i) reverse transcribing the RNA molecule to generate a deoxyribonucleic acid (DNA) molecule from said RNA molecule, wherein said DNA molecule comprises said barcode, and (ii) amplifying the DNA molecule to produce one or more amplicons, wherein said one or more amplicons of said DNA molecule co-localize with said protein of interest and comprise said barcode; and
   (c) identifying said barcode within said cell, thereby identifying said protein of interest.

2. The method of claim 1, wherein amplifying the DNA molecule includes circularizing the DNA molecule to generate a circular DNA molecule; and performing rolling circle amplification (RCA) on said circular DNA molecule to produce said one or more amplicons.

3. The method of claim 1, wherein identifying the barcode comprises detecting the one or more amplicons.

4. The method of claim 1, wherein the protein of interest is localized in or to a subceullar component.

5. The method of claim 1, further comprising, prior to (a), expressing the RNA molecule within the cell, wherein expression of the RNA molecule within the cell is controlled by one or more members selected from the group consisting of an inducible promoter, a cell type-specific promoter and a signal-specific promoter.

6. The method of claim 1, further comprising, prior to (a), delivering the RNA molecule directly to the cell.

7. The method of claim 1, wherein said RNA binding domain is a MS2 domain, a lambda phage N peptide, or a P22 phage N peptide.

8. The method of claim 1, further comprising, prior to (a), contacting said cell with a matrix-forming material to form a matrix.

9. The method of claim 8, wherein said matrix-forming material permeates throughout said cell.

10. The method of claim 8, wherein said matrix-forming material comprises polyacrylamide, cellulose, alginate, polyamide, agarose, dextran, or polyethylene glycol.

11. The method of claim 8, wherein said DNA molecule or one or more amplicons are attached to said matrix.

12. The method of claim 8, wherein said DNA molecule, or said one or more amplicons are modified with a functional moiety.

13. The method of claim 12, wherein said functional moiety is crosslinked, copolymerized, or non-covalently attached to said matrix.

14. The method of claim 13, wherein said functional moiety is an amine, an acrydite, an alkyne, a biotin, an azide, or a thiol functional moiety.

15. The method of claim 4, wherein said subcellular component is a cell membrane, a nucleus, or a synapse.

16. The method of claim 1, wherein said barcode comprises a nucleic acid sequence that is specific to said protein of interest, and wherein (c) comprises sequencing said one or more amplicons to identify said protein of interest.

17. The method of claim 1, wherein said RNA binding domain is fused in frame to said protein of interest internally, at an N-terminus, or at a C-terminus of said protein of interest.

18. The method of claim 1, wherein said RNA binding domain is an RNA recognition motif, a zinc finger domain, a KH domain, or a double-stranded RNA binding motif.

19. The method of claim 1, further comprising, in said step (b), removing said RNA molecule by a nuclease or a restriction enzyme.

* * * * *

```
                        SEQUENCE LISTING

<160> NUMBER OF SEQ ID NOS: 7

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcttcagcgt tcccgaga                                                 18

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
gtgtatcctg atcaaaaaag gugcgcugac aaagcgcgcc tttttt                  46

<210> SEQ ID NO 3
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
gtgtatcctg atcaaaaaag gugcgcugac aaagcgcgcc tttttgatc aggatacac     59
```

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tctcgggaac gctgaaga                                                 18

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
aaaaaaggug cgcugacaaa gcgcgccttt tttgatcagg atacac                  46

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatcaggata cac                                                      13

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tctcgggaac gctgaagaga tcaggataca c                                  31

UNITED STATES PATENT AND TRADEMARK OFFICE
CERTIFICATE OF CORRECTION

PATENT NO. : 10,179,932 B2
APPLICATION NO. : 15/325577
DATED : January 15, 2019
INVENTOR(S) : Church et al.

Page 1 of 1

It is certified that error appears in the above-identified patent and that said Letters Patent is hereby corrected as shown below:

In the Specification

Under STATEMENT OF GOVERNMENT INTERESTS
Column 1, Line 23:
Please delete:
"This invention was made with Government support under grant number 1U01MH098977-01 awarded by NIMH, grant number DE-FG02-02ER63445 awarded by DOE, and R01 MH103910-01 awarded by NHGRI. The Government has certain rights in the invention."
And insert:
-- This invention was made with government support under MH098977 and MH103910 awarded by the National Institutes of Health, and DE-FG02-02ER63445 awarded by the U.S. Department of Energy. The government has certain rights in the invention. --

Signed and Sealed this
Third Day of November, 2020

Andrei Iancu
*Director of the United States Patent and Trademark Office*